United States Patent [19]

Lipsky et al.

[11] Patent Number: 4,490,138
[45] Date of Patent: Dec. 25, 1984

[54] PHARYNGEAL SUCTION DEVICE

[76] Inventors: Steven Lipsky, 7720 Foothills Dr. S., Paradise Valley, Ariz. 85253; John D. Dale, 1211 W. Rovey, Phoenix, Ariz. 85013

[21] Appl. No.: 417,044

[22] Filed: Sep. 13, 1982

[51] Int. Cl.³ .............................................. A61M 7/00
[52] U.S. Cl. ................................. 604/40; 285/7; 403/354; 604/264; 604/268
[58] Field of Search ............... 403/345, 353, 354; 285/177, 239, 175, DIG. 22, 370, 397, 7; 433/91, 93; 604/118, 119, 902, 40, 264, 268, 275, 279, 280, 93, 158, 164

[56] References Cited

U.S. PATENT DOCUMENTS

| | | | |
|---|---|---|---|
| 1,518,211 | 12/1924 | Mave | 604/275 |
| 2,130,406 | 9/1938 | Angell | 433/91 |
| 2,531,730 | 11/1950 | Henderson | 433/91 |
| 3,321,087 | 5/1967 | Fuge et al. | 210/459 |
| 3,335,727 | 8/1967 | Spoto | 604/119 |
| 3,430,631 | 4/1969 | Abramson | 128/350 |
| 3,584,901 | 6/1971 | Willinger | 285/177 |
| 3,656,485 | 4/1972 | Robertson | 128/349 |
| 3,781,941 | 1/1974 | MacFarland | 285/7 |
| 3,807,401 | 4/1974 | Riggle et al. | 128/277 |
| 3,848,604 | 11/1974 | Sackner | 128/350 |
| 3,911,919 | 10/1975 | Raitto | 604/119 |
| 3,945,385 | 3/1976 | Sackner | 128/350 |
| 4,068,664 | 1/1978 | Sharp et al. | 433/91 |
| 4,221,220 | 9/1980 | Hansen | 128/276 |
| 4,257,629 | 3/1981 | Maple et al. | 285/177 |
| 4,266,813 | 5/1981 | Oliver | 285/177 |

FOREIGN PATENT DOCUMENTS

| | | |
|---|---|---|
| 258116 | 3/1883 | Fed. Rep. of Germany . |
| 2027261 | 12/1970 | Fed. Rep. of Germany ...... 285/177 |
| 1060415 | 4/1954 | France ............................ 403/103 R |

OTHER PUBLICATIONS

Super Sucker advertisement.
Suction Catheters, Health Devices, Apr. 1977, p. 134.

Primary Examiner—C. Fred Rosenbaum
Assistant Examiner—J. L. Kruter
Attorney, Agent, or Firm—Warren F. B. Lindsley

[57] ABSTRACT

A pharyngeal suction device for use during cardiopulmonary resuscitation and trauma stabilization. A hollow wand is provided with peripheral recesses which act as safety vents when the wand is used without the safety tip. The safety tip is attached to the wand in either of two orientations and secured at the peripheral recesses. A safety tip outlines a hemispherical surface and defines three passages which communicate with the interior of the wand.

4 Claims, 8 Drawing Figures

U.S. Patent  Dec. 25, 1984  4,490,138

PHARYNGEAL SUCTION DEVICE

BACKGROUND OF THE INVENTION

This invention generally relates to emergency medical instruments and more specifically to oral and pharyngeal suction devices which are used to remove vomitus, blood and foreign material from the mouths and pharynges of patients during cardiopulmonary resuscitation or trauma stabilization.

Suction devices of various designs are used during many medical procedures. The devices generally utilize a vacuum source, a collection container, and associated tubing. More specifically, a vacuum is effected within the collection container by means of the vacuum source. One end of a flexible connecting tube is connected to the collection container and the other end of the tube is attached to a suction tip which is used to remove debris and fluids from cavities in the patient's body.

During cardiac arrest the victim's stomach contents may be regurgitated and fill the hypopharyngeal, oropharyngeal, nasopharyngeal, and oral cavities. This may occur spontaneously or during resuscitative efforts when repeated tracheo-esophageal insufflation causes reflex emptying of an over distended stomach. If the victim has recently eaten, as is frequently the case, the vomitus emptied from the stomach contains large pieces of poorly chewed and undigested food ½ inch in diameter or larger. Before effective resuscitation can be accomplished, the victim's throat must be cleared of foreign matter and an open airway established.

In such situations the end of the suction device must be inserted into the patient's mouth and oro/hypopharynges in order to remove vomitus from the area of the epiglottis, glottis and hypopharyngeal sphincter. All of the above mentioned tissues are delicate and easily injured.

Prior suction devices are sometimes provided with a tube or wand located at the end of the suction hose to allow the open end of the tubing to be inserted into the field of operation, or through the oropharyngeal cavity. Present designs of such devices suffer at least three shortcomings.

First, the vacuum delivered to the end of the tubing or wand must be rather substantial to enable the extraction of debris and vomitus. However, this causes a dangerous condition in that in some circumstances the end can easily come into contact with healthy but delicate tissues, i.e. organs in the oropharyngeal and hypopharyngeal cavity. The suction causes the edges of the tube or wand to be drawn into the tissue surface while the tissues themselves are partially drawn into the inner bore of the wand, causing "vacuum injuries".

Typical kinds of attempts to avoid such conditions may be seen in U.S. Pat. No. 3,848,604, to Sackner; U.S. Pat. No. 3,945,385, to Sackner; U.S. Pat. No. 4,022,218, to Riddick; and U.S. Pat. No. 4,221,220, to Hansen. In all such examples the wand or tube is provided with a number of holes around its perimeter at a location adjacent to the influent end. Such holes prevent a full vacuum from being developed at the influent end of the wand even if the end is inadvertently blocked by tissue. However, this compromises the ability of the device to create full suction under normal conditions. Further, the peripheral holes are relatively small and thus can become clogged with debris. Once clogged, the aforementioned safety effect of the peripheral holes is defeated and the possibility of damage to the tissues increases.

The second type of attempt to avoid damage due to vacuum injuries can be seen in U.S. Pat. No. 3,321,087, to Fuge and Garber, although it is specifically designed for harvesting allantoic fluid. A similar design approach is used in the construction of the aspirator commonly used by dentists. In each case the end of the suction device is provided with a structure having a multiplicity of small, uniform perforations. These perforations tend to prevent damage to tissue since it is unlikely that they would all be entirely covered by a tissue surface at the same time. However, because of their small size, large pieces of debris cannot be removed through the suction device. These devices are designed to act as strainers and cannot be used to clear the vomitus, and particularly, large chunks of food or clotted blood. Even small pieces of debris can clog the perforations and render those suction devices inoperative.

Second, all the above mentioned devices use tubing and wands of relatively small inner diameter and inner passages. This makes them unsuitable for cleaning the oro and hypopharynges during cardiopulmonary resuscitation or trauma stabilization since the inner passages will become clogged by large pieces of vomitus and debris.

Third, few of the devices in the prior art are compatible with vacuum and collection systems designed for other suction devices. This makes it necessary for hospitals to purchase and maintain a special system for each type of suction device.

In conclusion, all of the devices in the prior art have serious shortcomings and are especially unsuited for use during cardiopulmonary resuscitation.

Thus it is an object of the present invention to provide a suction device especially suited for clearing the oro and hypopharynges during cardiopulmonary resuscitation or trauma stabilization.

It is a further object of the present invention to provide a suction device which will not damage even delicate tissues in the area of use, but which will remove semi-solid and solid material of relatively large size.

It is a further object of the present invention to provide a suction device which resists clogging.

It is another object of the present invention to provide a suction device utilizing a wand which may be used with or without a locking tip guard, depending on the trauma involved and the size of the debris to be removed.

It is still another object of the present invention to provide a suction device having a tip which can be selectively oriented before being locked in place.

It is another object of the present invention to provide a suction device which provides a means for visually orienting the device into a preferred position for insertion into the oropharyngeal cavity.

It is another object of the present invention to provide a suction device which may be used with a variety of vacuum and collection apparatus.

SUMMARY OF THE INVENTION

In keeping with one aspect of this invention, a suction device is constructed with a hollow tube having an open influent end for receiving material and an open effluent end for receiving a vacuum source. A tip guard extending longitudinally out from the influent end of the tube prevents material or tissue from blocking the influent end. The tip guard has three elongated arcuate members meeting at the major axis of the tube with open passages between them to form a generally hemispherical surface over the open influent end. The tip guard can be positioned so that the orientation of the arcuate members and open passages most effectively correspond to orientation of the cavity to be suctioned before the tip guard is locked in place.

The above mentioned and other features of this invention and the manner of obtaining them will become more apparent, and the invention itself will be best understood by reference to the following description of an embodiment of the invention taken in conjunction with the accompanying drawings.

DETAILED DESCRIPTION OF THE INVENTION

Figure 2:
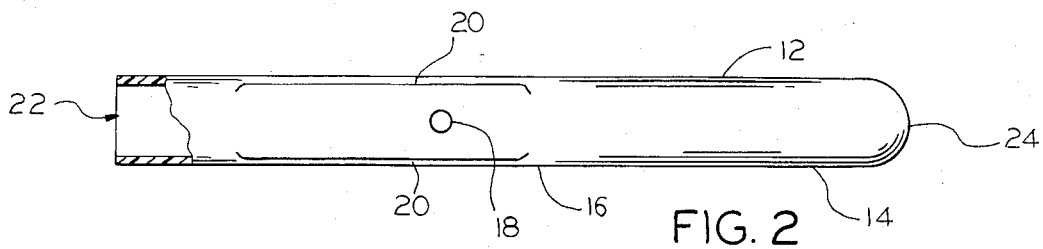
FIG. 2 is a plan view of the wand with the attached tubing shown in cross section.
Figure 1:
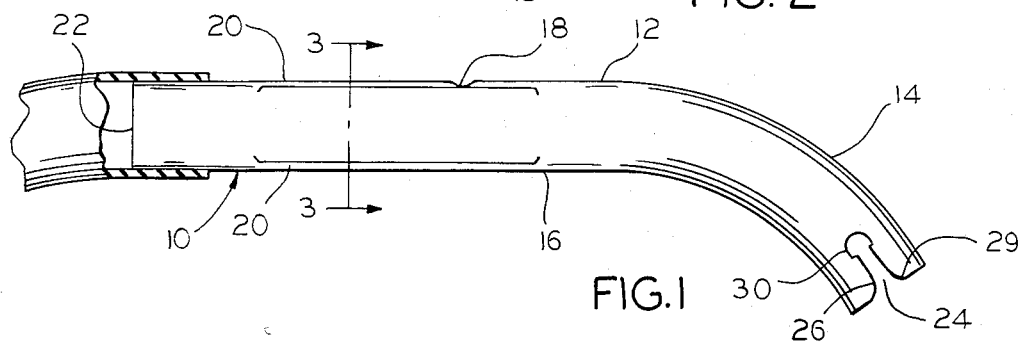
FIG. 1 is an elevational view of the wand.
Figures 3, 8:
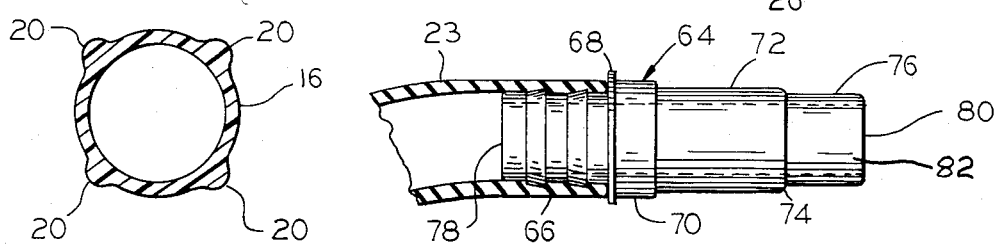
FIG. 3 is a cross-sectional view of the wand about line 3—3 of FIG. 1.
FIG. 8 is an elevation view of the universal adaptor with the attached tubing shown in cross section.
Figure 5:
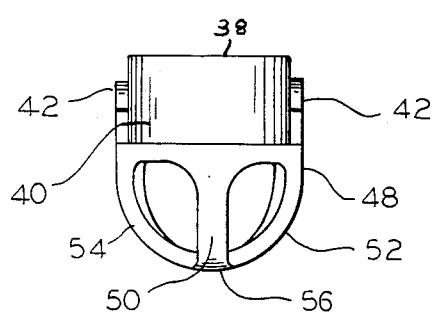
FIG. 5 is a plan view of the tip guard.
Figure 6:
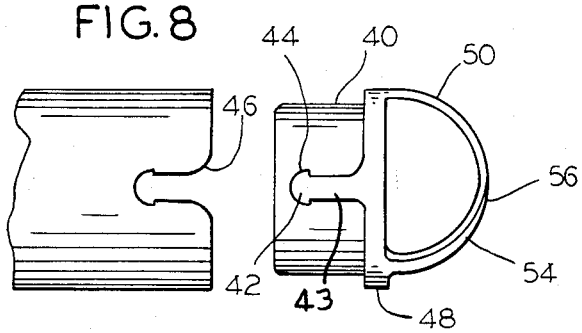
FIG. 6 is an enlarged elevational view of the side of the tip of the guard and wand.
Figure 4:
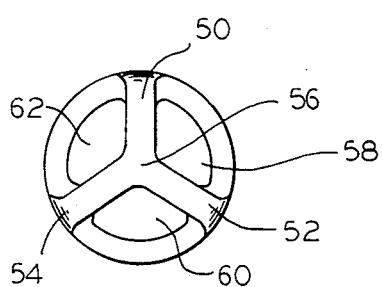
FIG. 4 is a elevational view of the front of the tip guard.

As shown in FIGS. 1-3 a wand 10 constructed in accordance with the teaching of this invention comprises a tube 12 having a curved section 14 and straight section 16.

The straight section 16 is provided with a means with which to regulate the effective vacuum available at the tip of the wand by aperture 18. The aperture acts as an air bleed and is operated by placing a finger over the aperture. When the aperture is covered, the maximum effective vacuum is available at the tip of the wand. When the aperture is uncovered, air bleeds into the device through the aperture 18 and reduces the vacuum available.

The straight section is also provided with ribs 20 as a means to provide a handle or gripping surface which will not be slippery when the medical technician using it is wearing surgical gloves or the surface is contaminated with slippery surgical debris or vomitus.

The effluent end 22 of the wand is connected to a conventional collection system, including a collection container and vacuum source, (not shown) via a flexible connecting tube 23. The flexible tube should be dimensioned so that its inner diameter is at least as large as the inner diameter of the wand to insure that any debris flowing through the wand will pass freely into the connecting tube. Of course, the effluent end and flexible tube may be joined by more complex means, such as a threaded connector. As is more fully described below, the other end of the flexible tube is connected to a collection container by means of a universal adaptor shown in FIG. 8.

Figure 7:
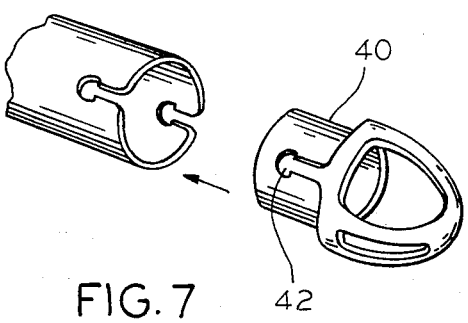
FIG. 7 is a perspective view of the tip guard and wand.

The curved section 14 of the wand extends from the straight section to the influent end 24. The influent end is provided with two peripheral recesses 26. The recesses are positioned 180° apart along the periphery of the influent end, as can best be seen in FIG. 7. The peripheral recesses serve two purposes.

First, they are a means of providing safety vents when the wand is used without the tip guard. They prevent damage to tissue if the influent end is lodged up against a tissue surface since the flow of air, liquids, and debris will be maintained through the vents. Hence, the tissue surface will not be drawn into the wand and the edges of the wand will not be urged into the tissue by the vacuum and damage the tissue.

These vents are less likely to become clogged with debris than are the holes of the devices in the prior art since they are connected by locating tapers 28 with the influent end. Debris lodged against the vent area will be drawn by the vacuum toward the wider section of the vent and then through the influent end. Thus, the smaller pieces of debris which easily clogged prior art devices will not clog the present invention.

Second, the peripheral recesses provide a means of guiding and securing a tip guard onto the influent end of the wand.

During cardiac arrest the victim's stomach contents are frequently regurgitated and fill the hypopharyngeal, oropharyngeal, nasopharyngeal, and oral cavities. This may occur spontaneously during resuscitative efforts when repeated tracheo-esophogeal insufflations cause reflex emptying of an over-distended stomach. The earliest priority is to clear the victim's throat of foreign material and establish an open airway to allow air exchange. If the victim has recently eaten, or become arrested from a massive upper gastrointestinal bleed or from a foreign body, the vomitus/blood in the hypo and oropharyngeal areas can contain large pieces of material greater than or equal to ½ inch in diameter. This blocks the airway and creates the danger of aspiration of foreign/contaminated material into the lungs.

Accordingly, the invention includes a tip guard shown in FIGS. 4-7. The guard 38 is provided with sleeve 40 which has an outside diameter equal to the inside diameter of the influent end 24 of the wand. Two bosses 42 extend from the sleeve and are preferably spaced 180° apart on the circumference of the sleeve. The bosses 42 are dimensioned so as to engage the detents 30 extending into the recesses when the sleeve is inserted into the influent end of the wand. The bosses are guided into the detents by the interaction between the curved leading edge 44 of the boss and the convex edges 46 of the peripheral recess. The large radius of curvature of the convex edge facilitates connection of the tip guard to the wand. The bosses 42 include necks 43. These bosses and necks are dimensioned to match the peripheral recess so that a smooth surface is formed around the circumference of the wand when the tip guard is in place. Once the bosses are engaged by the detents, the tip is locked into position and will not disengage during use.

The guard also has a collar 48 which preferably is dimensioned so that its outer diameter is equal to the outer diameter of the wand. Also, the distance from the collar 48 to the boss matches the distance from the influent end 24 of the wand to the detent 30. Hence when the tip guard is attached to the wand, the collar will abut the influent end. Since the outer diameter of the tip guard and wand are the same, a smooth continuous surface is formed which will not injure tissues.

Three arcuate members 50, 52, 54 extend from the collar 48 to a central dome area 56. The arcuate members and the dome define passages 58, 60 and 62. In the embodiment illustrated, the arcuate members, the passages and central area outline a hemispherical surface. Of course, the components may be dimensioned to other curved shapes such as a parabolic surface. The surface also could be in the form of a paraboloid which would fit onto a wand having an ellipsoidal cross-section.

It will be noted that the passages defined are large and allow passage of large pieces of material. In the embodiment shown, the area and the configuration of a given passage approximates, but is slightly smaller than, the inner diameter of the wand. Almost all material which is small enough to pass through the suction device will pass through the passages, but larger material, which could clog the device, will not.

The tip guard is desirably constructed so that arcuate member 50 is located 90° away from each of the bosses. Since both the bosses 42 and the detents are located 180° away from each other, the tip guard 38 may be inserted into the wand in either of two orientations. In the preferred orientation (as shown) the arcuate member 50 is positioned adjacent to the top of curved section 14 while passage 60 is positioned adjacent the bottom of the curved section. Alternatively, guard 38 can be rotated to change the orientation of members 50 relative to the curved section if the condition of the patient or other considerations warrant.

This selective orientation facilitates the use of the suction device. When the device is used in most cardiopulmonary resuscitation applications, the guard is attached to the wand so that the member 50 is adjacent to the upper surface of the curved section. In that orientation the member 50 will be adjacent to the posterior wall of the oropharyngeal cavity. Its curved surface helps the operator move the suction device down through the pharynges. Also, in this orientation the passage 60 will be adjacent to the anterior wall of the pharynx and straddle the epiglottis. This assures that the area of the epiglottis is swept clear of vomitus.

In this orientation the member 50 also acts as a visual guide. By orienting the wand so that the member 50 is pointed toward the roof of the patient's mouth, the technician will be assured that the plane of the curve of the wand is aligned with the plane of the curve of the oral/pharyngeal passage and that the suction device may be inserted correctly and smoothly without damage to tissue.

Other embodiments of the invention are contemplated. For example, the wand and tip may be constructed as a single integral unit, although some of the features of the invention would not be needed in such an embodiment, such as the bosses and recesses. Also, versions of the device scaled down in size are contemplated for use in treatment of children and infants.

The wand and tip guard components are preferably constructed from a resilient material which can be sterilized, such as ABS plastic. In the illustrated embodiment of the invention which is in the adult version, the inner diameter of the wand 10 and the outer diameter of the sleeve 40 are 0.750 inches. The outer diameter of the wand is 0.890 inches. The straight section is 5 inches long. The curved section 14 extends over an arc of 60° and has a radius of curvature of 3.5 inches. The aperture is 0.25 inches in diameter.

As with most suction devices, the present invention must be connected to a collection system (not shown). Such systems include a collection container connected to a vacuum source by a port at the top of the container. The flexible tube 23 leading to the effluent end 22 of the wand is connected to another port in the container. The vacuum source draws fluid and debris into the collection container where it is stored until emptied.

The collection systems presently owned by hospitals and paramedic teams are compatible with the present invention. Most collection containers have an influent port for receiving debris from the suction device, a vacuum port connected by tubing to the vacuum source, and an emptying port which is usually larger than the other ports and is capped when the suction device is in use. When the contents of the container are to be removed, the emptying port is uncapped and the contents are poured out. The emptying ports vary in size according to the manufacturer of the collection container. The present invention uses a universal adaptor shown in FIG. 8 to connect the suction device to existing collection systems through the emptying port. The former influent port is then capped. Different manufacturers have designed their collection jars with emptying ports of various diameters.

The adaptor 64 has a ribbed, tube connector 66 which receives tube 23, abutment 68, intermediate section 70, first conical portion 72, step 74, and second conical portion 76. The influent end 78 and effluent end 80 of adaptor 64 communicate by passage 82.

The conical portions 72 and 76 are inserted into the emptying ports of collection containers presently in use. The first conical section increases from a diameter of 0.990 inches to a diameter of 1.080 inches and will mate with ports having an inner diameter of 1.0 inch. The second conical section increase from a diameter of 0.870 inches to a diameter of 0.885 and will mate with a port having an inner diameter of 14/16th of an inch (0.875 inches). The intermediate section 70 has an outer diameter of 1.125 inches (1⅛ inches).

The universal adaptor allows the device to be used with the following hospital systems which utilize disposable collection jars: KG2 IPS, KGF 16PS-72 and EZ 12C systems manufactured by Sorensen Research Co.; the CRD System manufactured by Medivac Corporation; Argyll's "Sep-T-Vac" System; and Bard-Parker's "Vac-Rite" System which is manufactured by Medical Development Corporation. It also can be used with the Portable Laerdal Suction Unit sold by Laerdal Medical Corporation of Armonk, N.Y.

While the principles of the invention have been described in connection with specific apparatus and application, it is to be understood that this description is made only by way of example and is not as a limitation on the scope of the invention.

We claim:
1. A suction device comprising:
a hollow tube having an open influent end and an open effluent end for communicating with a vacuum and collection system,
said tube being provided with recesses in the tube extending from the influent end of the tube toward the effluent end to prevent a full vacuum from being formed within the tube and to permit continued suction when the influent end of the suction device is blocked.
a tip guard for attachment to said influent end of said tube,
said tip guard comprising a hollow sleeve having a collar at one end, the other end of said sleeve being slidably movable within the influent end of said tube with the collar being positioned adjacent the end of the tube, said sleeve being provided with a pair of longitudinally extending boss means spacedly positioned to extend outwardly from the surface of said sleeve for longitudinally slidably moving into the recesses of the end of the tube when the sleeve is moved into the tube until said collar engages the end of the tube, and three elongated arcuate members each having one end attached to said collar with each of the other ends of the arcuate members joined together at the major axis to outline a substantially hemispherical surface over the influent end of the tube, said members defining three passageways therebetween through which material may pass into the influent end of the tube.

2. The suction device set forth in claim 1 wherein:
said hollow tube is curved at its influent end, and
said effluent end of said tube is provided with a plurality of ribs spacedly arranged around the outer periphery of said tube in a direction longitudinally of said tube.

3. A safety tip guard for use with a pharyngeal suction device for use during cardiopulmonary resuscitation for ttauma stabilization comprising:

a longitudianl resilient tube having an influent end with two longitudinal recesses, the recesses having detent means distal from the influent end of the resilient tube, a tip guard having a collar at one end and hollow sleeve at the other end with said sleeve end slidably movable within said influent end of the tube with said collar positioned adjacent of the end of the tube, said sleeve being provided with a pair of bosses spacedly positioned to extend outwardly from the exterior surface of said sleeve for slidably moving into the recesses of the end of the tube when the sleeve is moved into the tube until said collar engages the recessed end of the tube, and three elongated arcuate members each having one end attached to said collar with each of the other ends of the arcuate members joining together at the major axis to outline a substantially hemispherical surface over the influent end of the tube, said members defining three passageways therebetween through which material may pass into the influent end of the tube.

4. The safety tip guard set forth in claim 3 wherein:
said bosses are formed 180 degrees aparat and of a resilient material which substantially fill the associated recesses in the influent end of the tube and interlock therewith when said tip guard is mounted thereon.

* * * * *

UNITED STATES PATENT OFFICE
CERTIFICATE OF CORRECTION

Patent No. 4,490,138          Dated December 25, 1984

Inventor(s) Steven Lipsky and John D. Dale

It is certified that error appears in the above-identified patent and that said Letters Patent are hereby corrected as shown below:

Claim 3, line 3, delete "ttauma" and substitute ---trauma---;

Claim 3, line 4, delete "longitudianl" and substitute ---longitudinal---;

Claim 3, line 8, after "and" insert ---a---.

Signed and Sealed this

Sixteenth Day of April 1985

[SEAL]

Attest:

DONALD J. QUIGG

Attesting Officer      Acting Commissioner of Patents and Trademarks